United States Patent [19]

Bram et al.

[11] Patent Number: 5,523,227
[45] Date of Patent: Jun. 4, 1996

[54] DNA ENCODING CALCIUM-SIGNAL MODULATING CYCLOPHILIN LIGAND

[75] Inventors: Richard J. Bram, Memphis, Tenn.; Gerald R. Crabtree, Woodside, Calif.

[73] Assignee: The Board of Trustees of the Leland Stanford Junior Univ., Stanford, Calif.

[21] Appl. No.: 261,662

[22] Filed: Jun. 17, 1994

[51] Int. Cl.$^6$ ............................... C12N 5/08; C12N 15/12
[52] U.S. Cl. ........................................ 435/240.2; 536/23.5
[58] Field of Search .................. 536/23.5; 435/172.3, 435/320.1, 240.2, 172.1

[56] References Cited

PUBLICATIONS

Friedman et al., "Cloning and Characterization of Cyclophilin C–Associated Protein: A Candidate Natural Cellular Ligand for Cyclophilin C," Proc. Natl. Acad. Sci. USA (1993) 90:6815–6819.

Friedman and Weissman, "Two Cytoplasmic Candidates for Immunophilin Action Are Revealed by Affinity for a New Cyclphilin: One in the Presence and One in the Absence of CsA," Cell (1991) 66:799–806.

Primary Examiner—Mindy Fleisher
Assistant Examiner—Terry A. McKelvey
Attorney, Agent, or Firm—Bertram I. Rowland

[57] ABSTRACT

DNA and protein compositions are provided for calcium-signal modulating cyclophilin ligand which are shown to act in the calcium-dependent pathway for activation of a number of genes. The DNA composition and proteins may be used in investigating the processes associated with calcium-dependent activation of genes, as well as screening of drugs for interaction with the subject proteins for modulating cell processes, e.g. T-cell activation.

5 Claims, 4 Drawing Sheets

DNA ENCODING CALCIUM-SIGNAL MODULATING CYCLOPHILIN LIGAND

This invention was made with Government support under Contract No. IN-176-C awarded by the American Cancer Society and Contract No. CA 21765 awarded by the National Institutes of Health. The Government has certain rights in this invention.

INTRODUCTION

1. Technical Field

The field of this invention is transcription regulation and its use.

2. Background

There is extensive interest for a wide variety of purposes in understanding how a cell responds to agents in the environment. In one mechanism, agents in the environment bind to surface membrane proteins, which by themselves or in combination with other proteins, are able to institute a cascade of events. These events may involve a plurality of proteins, where inactivation or activation of various components in the cascade ultimately results in binding of a protein to a DNA sequence with initiation of transcription of one or more genes. Included in this cascade are phosphatases, kinases, complexing proteins, proteases, DNA binding proteins, as well as other factors.

One pathway requires calcium influx, from extra- or intracellular sources, as a secondary signal, which is necessary, but not sufficient, to provide the signal necessary to initiate transcription. A number of proteins have been associated with the pathway involving calcium, such as calmodulin, calcineurin, CaM kinase, etc. The increased cytoplasmic calcium concentration may be as a result of external influx or release of internal stores. The mechanism by which enhanced calcium concentration acts in conjunction with other agents to signal the initiation of transcription is not completely understood. However, it is clear that the pathway involving the calcium signal is important to a number of processes involved with activation and proliferation of cells of interest.

One cell population of interest is muscle cells, particularly cardiac muscle cells. The ability of these cells to perform work and the regulation of these cells is of extreme importance to heart function. Coronary vasodilators, such as verapamil, find ,extensive use in the treatment of cardiac malfunction. By being able to regulate calcium flow to which the heart cells are responsive, improved regulation of heart function may be achieved.

Another cell population of particular interest are T-cells, the primary component of the cellular arm of the immune system. T-cell activation results from stimulation of the T-cell receptor by binding of the T-cell receptor to an antigen presenting cell. The immunosuppressant drug cyclosporin A (CsA) blocks a calcium-dependent signal from the T-cell receptor (TCR) that normally leads to expression of the T-cell growth factor interleukin-2 (IL-2) and other lymphokines, and ultimately to T-cell activation. CsA binds to and inhibits the prolyl isomerase activity of cyclophilin. This drug-isomerase complex inactivates the $Ca^{2+}$-dependent phosphatase, calcineurin, by a direct interaction near the active site of the enzyme. (Lieu et al., *Cell* 66, 807–15 (1991); Clipstone and Crabtree, *Nature* 357, 695–7 (1992); and O'Keefe et al., *Nature* 357, 692–4 (1992).)

Calcium intracellular levels play a major function in a number of different cells involving a number of different activities. In addition to the induction of gene transcription by calcium influx, many other calcium influxes, such as muscle contraction (both cardiac and skeletal), vesicle degranulation (such as in the response of neutrophils and macrophages to infection, or basophil response to antigen stimulation, or release of acetylcholine by neurons), and closure of intracellular gap junctions offer opportunities for cellular regulation. Some of the responses may not require calcium induced transcription, but are instead probably due to a direct effect of calcium on intracytoplasmic proteins, such as troponin-tropomyosin in muscle contraction.

The cell cycle can also involve fluxes of calcium. Intracellular chelators which block changes in intracellular calcium concentration can block the cell cycle from progressing, thereby arresting cell division. (Rabinovitch et al., 1986, J. of Immunol. 137, 952–961). Therefore, regulation of calcium can be effective in modulating cell division in normal and diseased cells.

For many purposes, there is substantial interest in being able to selectively prevent activation of cells or enhance the activation of cells. For example, for heart muscle cells, one would wish to be able to maintain their coordinated action; for T-cell mediated autoimmune diseases, one would wish to inhibit the activation of T-cells involved in the autoimmune indication. For infections, there would be interest in being able to activate T-cells, to more rapidly respond to the pathogen. In the case of cancer, there is an interest in slowing the proliferation of the cancer cells, which may allow for therapies which are not as destructive to the host as present day therapies. In order to achieve agents, particularly synthetic organic compounds, which can serve various purposes in the activation or deactivation of cells, it is necessary to be able to isolate the components in the pathway. In this way, one can determine whether various agents will bind to the component and act to inactivate or activate the component.

In addition, as one understands the pathway more completely, one may be able to modulate the pathway more effectively, providing for agents which are selective for a particular set or subset of a cellular population. Since in many cases activation requires co-stimulation, being able to manipulate agents available to the cell may allow for such cellular activity. Furthermore, in understanding the pathway, it is frequently desirable to be able to selectively control the presence or the absence of a particular intermediate in the pathway. This can be achieved with knock-outs using homologous recombination, integration of genes providing for antisense sequences, introduction of expression constructs involving inducible promoters, and the like. There is also an interest in being able to determine when a particular gene is being expressed or is silent, the nature of the cells in which the protein is expressed, and the like. Therefore, there is substantial academic and commercial interest in identifying specific components of cellular pathways to allow for understanding the pathway, selectively modulating the pathway, and developing drugs which may be active in binding to the target protein.

Relevant Literature

The yeast 2-hybrid system is described in Chien et al., *Proc. Natl. Acad. Sci. USA* 88, 9578–9582 (1991); Durfee et al., *Genes Dev.* 7, 555–69 (1993). The role of NF-AT in T-cells for inducible expression of IL-2 is described in Emmel et al., *Science* 246, 1617–1620 (1989); Verwij et al., *J. Biol. Chem.* 265, 15788–15795 (1990); Karttunen and Shastri, *Proc. Natl. Acad. Sci. USA* 88, 3972–3976 (1991); and Mattila et al., *Emble J* 9, 4425–33 (1990). The role of p59fyn (Neg-Fyn) tyrosine kinase as evidenced by a dominant-negative form of the kinase is described in Kypta et al., *EMBO J* 7, 3837–3844 (1988); Twamley-Stein et al., *Proc. Natl. Acad. Sci. USA* 90, 7696–7700 (1993); and Samelson et al., *IBID* 87, 4358–4362 (1990). The role of Lck in T-cell activation is described by Straus and Weiss, *Cell* 70, 585–593 (1992). NF-IL-2A is described by Ullman et al., *Science* 254, 558–562 (1991).

SUMMARY OF THE INVENTION

A purified form of calcium-signal modulating cyclophilin ligand (CAML), its DNA sequence, and its role in the calcium activation pathway is described. The protein and DNA may be used for diagnostic purposes and for identifying agents for modulating the calcium induced activation pathway. Knowledge of the coding sequence allows for manipulation of cells to elucidate the mechanism of which CAML is a part.

DESCRIPTION OF SPECIFIC EMBODIMENTS

Figure 1A:
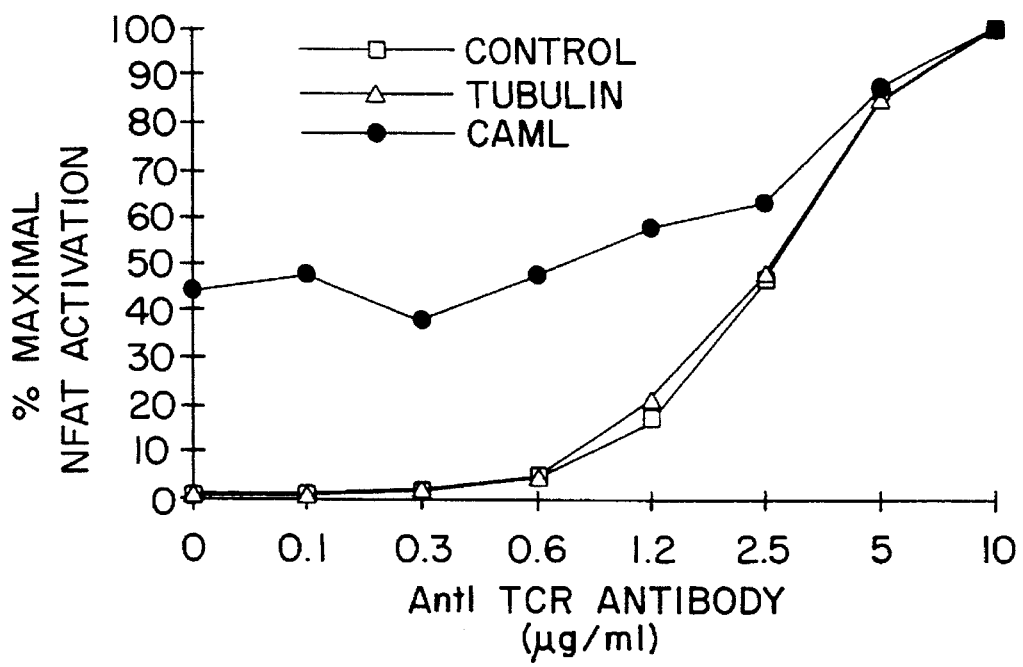
FIGS. 1a–d demonstrate activation of transcription by CAML overexpression in T cells. 1(a) is a graph comparing TCR-stimulation in cells co-transfected with a CAML-expressing cassette with cells which do not overexpress CAML. 1(b) is a graph showing the role of PMA in CAML induction of NF-AT activity with cells overproducing CAML and not overproducing CAML. 1(c) is a bar graph evaluating the effect of a p59fyn deficiency in a T cell on CAML T cell activation. 1(d) is a bar graph evaluating the effect of a Lck deficiency in a T cell on CAML T cell activation.
Figure 1B:
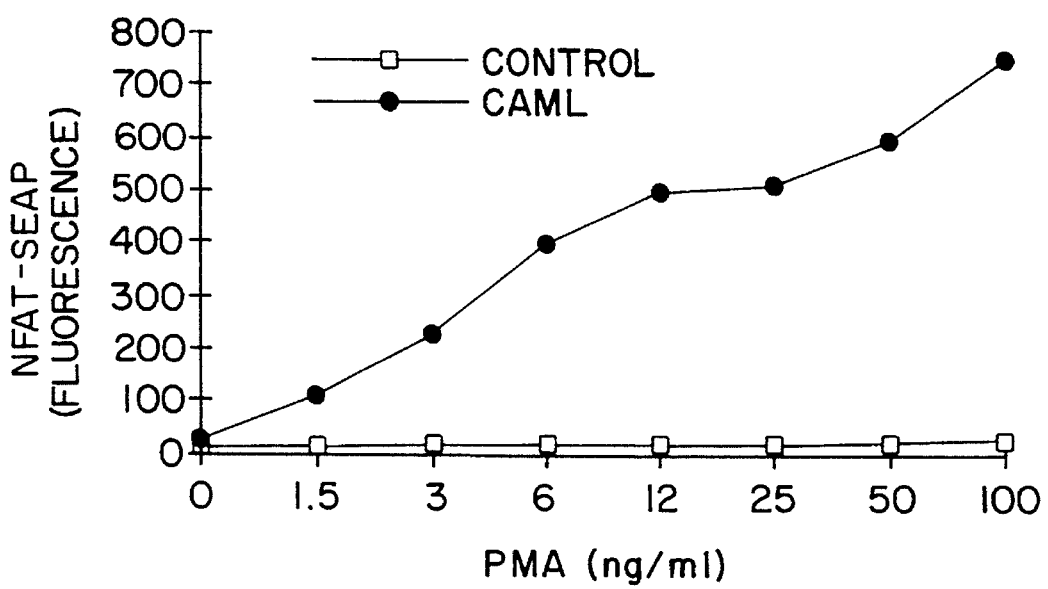
Figure 1C:
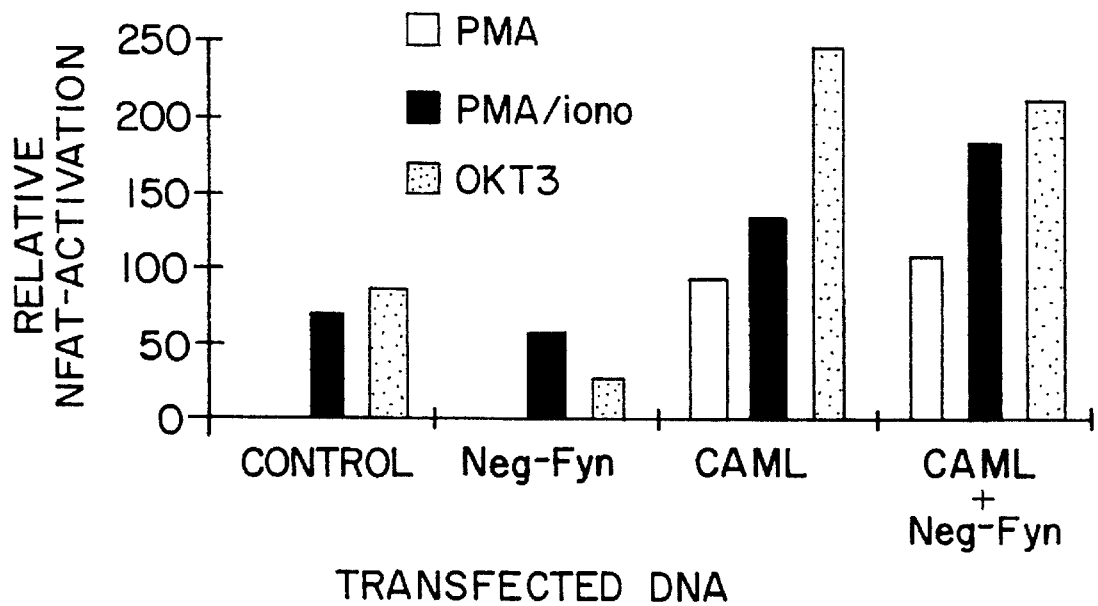
Figure 1D:
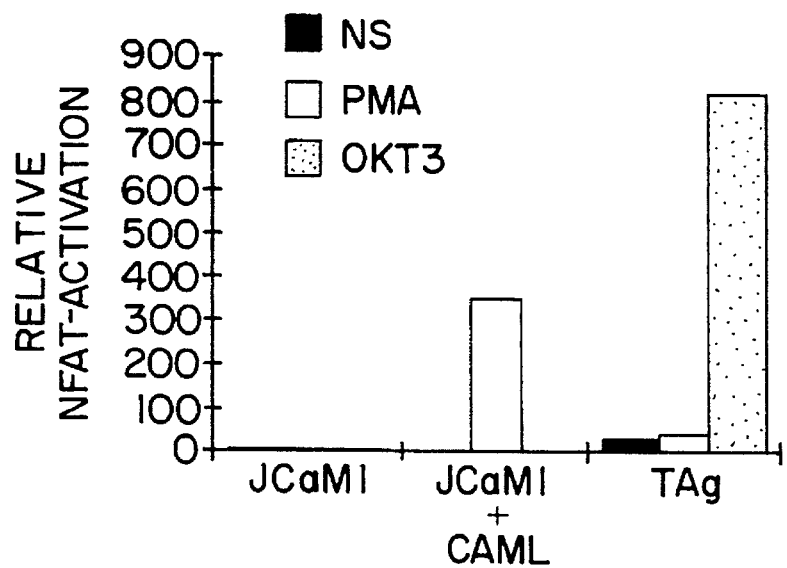

DNA and protein compositions, and fragments thereof, of calcium-signal modulating cyclophilin ligand (CAML), particularly human CAML, are provided. The DNA and protein compositions find use in screening for agonists and antagonists, in elucidating the role CAML plays in cellular signal transduction, the screening of cellular responses to external agents in relation to the expression of CAML, and the modulation of cellular responses associated with signal transduction involving CAML.

CAML DNA and protein have the following sequences.

DNA Sequence (SEQUENCE ID NO:1:)

| Sequence | Position |
|---|---|
| CGCCACTGCCACCCCTCCCAGACTGTGGACGGGAGG<u>AT</u>GGAGTCGATGGCCGTCGCTACC | 60 |
| GACGGCGGGGAGAGGCCGGGGGTCCCAGCGGGCTCAGGTCTGTCGGCTTCCCAGCGTCGG | 120 |
| GCGGAGCTGCGTCGGAGAAAGCTGCTCATGAACTCGGAACAGCGCATCAACCGGATCATG | 180 |
| GGCTTTCACAGGCCCGGGAGCGGCGCGGAAGAAGAAAGTCAAACAAAATCAAAGCAGCAG | 240 |
| GACAGTGATAAACTGAACTCCCTCAGCGTTCCTTCCGTTTCAAAGCGAGTAGTGCTGGGT | 300 |
| GATTCAGTCAGTACAGGAACAACTGACCAGCAGGGTGGTGTGGCCGAGGTAAAGGGGACC | 360 |
| CAACTGGGAGACAAATTGGACTCGTTCATTAAACCACCTGAGTGCAGTAGTGATGTCAAC | 420 |
| CTTGAGCTCCGGCAGCGGAACAGAGGGGACCTGACAGCGGACTCGGTCCAGAGGGGTTCC | 480 |
| CGCCATGGCCTAGAGCAGTACCTTTCCAGATTCGAAGAAGCAATGAAGCTAAGGAAACAG | 540 |
| CTGATTAGTGAAAAACCCAGTCAAGAGGATGGAAATACAACAGAAGAATTTGACTCTTTT | 600 |
| CGAATATTTAGATTGGTGGGATGTGCTCTTCTTGCTCTTGGAGTCAGAGCTTTTGTTTGC | 660 |
| AAATACTTGTCCATATTTGCTCCATTTCTTACTTTACAACTTGCGTACATGGGATTATAC | 720 |
| AAATATTTTCCCAAGAGTGAAAAGAAGATAAAGACAACAGTACTAACAGCTGCACTTCTA | 780 |
| TTGTCGGGAATTCCTGCCGAAGTGATAAATCGATCAATGGATACCTATAGCAAAATGGGC | 840 |
| GAAGTCTTCACAGATCTCTGTGTCTACTTTTTCACTTTTATCTTTTGTCATGAACTGCTT | 900 |
| GATTATTGGGGCTCTGAAGTACC<u>AT</u>GAAGCCTGTAGAACTGAGAAGGAGAAGCTTACGAA | 960 |
| AAAAATCCTCTTCTATATTGCAGTGTCTCTAAAGGAGGCAAATTGGTTTACACCTTCATG | 1020 |
| TAATTCTTTTACTTTAGGGGTTGTAAAGCTACTTTATTAGATATAGAATGGCAGATTCTC | 1080 |
| TGATTTAAAAGGGCTGAGTTTGTATTATTACTGATATGAAGAATAGAGTACCAATGTCAT | 1140 |
| TAATTGATTTTTCTTGTTAATCAGAATTCCTATTCTGTACCTTTCCTCTAACTTCTCAGA | 1200 |
| TTTGTAATTCTTCTTTTCGGGAGCTGAGCTAGTGCTTTTAGGAGAACAGATAAATGTGGT | 1260 |
| CTCAGCCAGCCCTAGAGACTGCTTCTTGTGTTTGTGTCATTCTGTCCTGAGAAATGAAGT | 1320 |

-continued

CATCTGAAAAATAAAAATGCAGAAACCCAAAAAAAAAAAAAAAAAAAAAAAAAAAAAAAA 1380

AAAAAAAAAAA 1391

Protein Sequence (SEQUENCE ID NO:2:)

| | |
|---|---|
| MESMAVATDGGERPGVPAGSGLSASQRRAELRRRKLLMNS | 40 |
| EQRINRIMGFHRPGSGAEEESQTKSKQQDSDKLNSLSVPS | 80 |
| VSKRVVLGDSVSTGTTDQQGGVAEVKGTQLGDKLDSFIKP | 120 |
| PECSSDVNLELRQRNRGDLTADSVQRGSRHGLEQYLSRFE | 160 |
| EAMKLRKQLISEKPSQEDGNTTEEFDSFRIFRLVGCALLA | 200 |
| LGVRAFVCKYLSIFAPFLTLQLAYMGLYKYFPKSEKKIKT | 240 |
| TVLTAALLLSGIPAEVINRSMDTYSKMGEVFTDLCVYFFT | 280 |
| FIFCHELLDYWGSEVP | 296 |

The DNA sequence comprising all or a portion of the coding region may be isolated and purified in conventional ways. The DNA sequence may be cDNA or genomic, and if genomic may include the 5' and/or 3' untranslated regions, e.g. the transcriptional initiation region comprising the promoter, enhancer, etc., or the transcriptional termination region, as well as flanking sequences. The DNA sequence is conveniently less than about 20 kbp, more usually less than about 10 kbp and at least about 18 bp, more usually at least about 30 bp. The DNA .sequence may include flanking sequences from the locus comprising the gene encoding CAML or include flanking sequences unrelated to the CAML locus, from the same or different host source or synthetic DNA.

The CAML proteins may be found in any mammalian cell and based on analogy to other proteins involved with transcription regulation involving calcium, would expected to be conserved over a wide variety of species. Thus, CAML proteins from other species will have at least about 60% homology with the human protein sequence, usually at least about 70% homology, as determined by conventional databank programs for determining homologous sequences, and may be present in domestic animals, laboratory animals, such as mice, rats and rabbits, pets, such as dogs, cats, and the like, etc.

The CAML protein will have a molecular weight of about 33 kDa, as evidenced by SDS-polyacrylamide gel migration and an open reading frame of 888 bp. The amino acid sequence has no obvious similarities to other known proteins, Three hydrophobic regions of > 20 residues each at the C-terminus fulfill the characteristics of transmembrane domains by the method of Sipos et al, *Eur. J. Biochem.* 213, 1333–1340 (1993). CAML is an integral membrane protein with a majority of the polypeptide on one side of the membrane, in accord with its role in calcium transport in regulation. The cDNA is about 1400 bp and the message is found in all tissues with the highest levels found in testis and brain. CAML's role has been elucidated in T cells, which is exemplary of other cells, e.g. muscle cells, brain cells, testes, ovaries, etc. In muscle cells, troponin regulates Ca-mediated muscle contraction.

CAML binds to cyclophilin B. Overexpression of CAML in T-cells partially abolishes the requirement for TCR crosslinking as evidenced by activation of NF-AT specific transcription, when assayed in the presence of phorbol ester (PMA) to provide a co-stimulatory signal. The degree of NF-AT activation by CAML varies from 20–125% of maximal induction—PMA plus ionomycin—in multiple transfections and is always distinctly different from controlled transfections, in which activation of NF-AT is not observed in cells stimulated by PMA alone.

Activation of NF-AT by CAML requires exogenous stimulation of PKC by PMA, unlike TCR mediated activation, which is alone sufficient to activate both calcium and PKC signal transduction pathways. CAML produces its effect in the calcium pathway downstream of the TCR and phospholipase C. CAML is capable of activating NF-AT in p59fyn and Lck tyrosine kinase defective cells. CAML mediated activation is completely abolished in the presence of immunosuppressive amounts of calcineurin inhibitors CsA and FK506. CAML partly replaces the calcium influx requirement for both NF-IL2A and the entire IL-2 enhancer, in a fashion similar to its effect with NF-AT. In both cases, the degree of stimulation varies from 20–60% of the maximal stimulation seen with PMA plus ionomycin treatment. Without CAML there is no detectable expression from NF-IL2A or the IL-2 enhancer in the absence of calcium ionophore. CAML overexpression has no effect on the calcium-independent transcription factor AP1.

CAML acts to elevate intracellular calcium by causing cytoplasmic influx of calcium, as evidenced by analysis by flow cytometry of calcium levels in CAML overexpressing cells.

The DNA gene sequence comprising the coding sequence for CAML can be used in a wide variety of ways. Fragments of 18 nt or greater up to the entire cDNA or limited to the open reading frame, may be used as probes to identify CAML genes in hosts other than human, to screen agents for their effect on CAML expression, to provide antisense sequences with an inducible promoter, so that CAML expression can be turned on and off to investigate cellular response to external agents, to express the CAML protein or fragment thereof, to express a fragment of CAML to act as a dominant negative, etc. If desired, the terminal portion of the protein involving the transmembrane sequences, which extend from nucleotide 598 to nucleotide 903 may be removed, so that the remaining truncated CAML may be provided as a soluble protein. Alternatively, microsomes may be prepared comprising CAML which may be used, where the CAML will then be associated with a lipid membrane. The DNA sequence may also be mutated to determine the sites essential for binding to cyclophilin B, as well as other sites associated with the influx of calcium into the cell. By employing mutagenesis, the regions essential for CAML activity can be determined for the development of agonists and antagonists.

Various transcription and expression constructs can be prepared. Thus, cassettes can be prepared comprising a promoter functional in the target host, all or a portion of the coding region of CAML in the sense or antisense direction, and a termination region for terminating transcription and expression, as appropriate. For inducible transcription, various enhancers may be employed. Depending upon whether constitutive or inducible transcription or expression is desired. Promoters of interest include SV40 promoter, β-actin promoter, β-gal promoter, λ-promoter, GAL1–GAL10 promoter, metallothionein I or II promoter, etc. Depending upon the purpose of the expression cassette, the target cells may be prokaryotic or eukaryotic, conveniently for expression employing E. coil, S. cerevisiae, CHO cells, COS cells, etc. For investigating the role of CAML, the host cells will usually be mammalian cells, particularly human cells, such as Jurkat T-cells, H9c2(2-1), rat heart myoblast (which fuse to form myotubes, which respond to stimulation by acetylcholine, Exp. Cell Res. 98:367–381, 1976), mouse C2C12, or other stable cell lines. In some instances one may wish to use primary cells.

The expression cassette may be introduced into the target cells in a wide variety of ways, frequently depending upon the nature of the particular target cells. For introduction of the DNA, one may use calcium phosphate precipitated DNA, transfection, using a wide variety of available viral vectors, electroporation, biolistics, fusion, or the like. The particular method for introducing the DNA into the host cell is not critical to this invention. In conjunction with the introduction of the cassette, various markers may be used, which allow for selection of cells comprising the expression cassette. For the most part, the markers will be antibiotic resistance genes, e.g. Neo, CAT, Tet, etc., or providing prototrophy to an auxotrophic host.

The DNA sequence may be used as a probe to identify expression of CAML in a target cell. The use of probes to identify a message is well established and does not require elaborate exemplification here. See, for example, Molecular Cloning: A Laboratory Manual, Sambrook et al., Eds., Cold Spring Harbor Laboratory, Cold Spring Harbor, N.Y., 1989. Particularly, RNases may be inactivated, and message RNA bound to a membrane surface. Labeled DNA sequence of the CAML cDNA may then be used under hybridization conditions to determine duplex formation by means of a label. Various labels may be used, which may be bound directly or indirectly to the nucleotide probe, such as fluorescers, radioisotopes, enzymes, and the like.

Of particular interest is introducing into a host cell the CAML expression cassette employing an inducible transcriptional initiation region, so that one may induce the expression of CAML at various levels, depending upon the amount of inducing agent one employs. In this manner, agents which are able to permeate the membrane into the cytoplasm may be screened as to their effect on the calcium activation pathway, in the presence or absence of CAML. One may use a cellular host, where the native CAML gene has been knocked out employing homologous recombination, in accordance with conventional techniques. See, for example, Chisaka and Capecchi (1991), Nature 350, 473–479; Koller and Smithies (1992), Ann. Rev. of Imm. 10, 705–730; Riele et al. (1990), Nature 348, 649–651. In this manner, one may investigate the effect agents have on muscle cells or T-cell activation in the absence or presence of CAML, so that agents may be evaluated for their ability to control cellular activation, e.g. inhibit the secretion of IL-2 or other cytokines in T-cells, in relation to the expression of CAML.

The CAML protein can be purified to a high level of purity, usually at least about 50% of total protein, preferably at least about 75%, more preferably at least about 95% or greater, up to substantially pure. The protein may be prepared and purified in accordance with conventional ways, expressing the protein in any convenient cellular host. The protein would then be purified by HPLC, gel exclusion chromatography, affinity chromatography, or the like. CAML may be used for the preparation of specific antibodies, which can be used in assays for detecting the presence of CAML as present in a cellular lysate or for affinity purification. Monoclonal antibodies can be prepared in accordance with conventional ways, where the CAML may be used as an immunogen to immunize a mouse or other laboratory animal for the production of antiserum. For monoclonal antibodies, the spleen may be isolated and splenocytes fused with an appropriate immortalizing cell or other agent, e.g. virus, and the resulting immortalized cells screened for the production of monoclonal antibodies specific for CAML.

The use of antibodies in diagnostic assays is amply exemplified in the literature. The cells or cellular lysate may be bound to a surface, labeled antibody added for binding to CAML, non-specifically bound antibody washed away, where the presence of label bound to the surface is indicative of the presence of CAML in the cell or cellular lysate. The proteins may also be used in a soluble or "insoluble" form (including the transmembrane sequences, either bound or unbound to a membrane) for screening agents capable of binding to CAML. In this way, one can identify candidates which may interfere with the binding of CAML to cyclophilin B, or otherwise inhibiting the role of CAML in the host cell.

As already indicated Ca plays a general regulatory role in many different cells. In addition to the cells previously discussed, in light of the high expression of CAML in testis and ovary, calcium can play a role in gametogenesis or function. The importance of calcium in sperm function is described by Hong et al., Lancet (1984 Dec.22) 2(8417–18):1449–51; Thomas and Meizel, In: Gamete Res. (1988 Aug.) 20(4):397–411; and Yanagimachi, In: Biol Reprod. (1978 Dec) 19(5):949–58. Also, CAML is highly expressed in brain. Calcium flux has been recognized as regulatory in brain, where calcineurin has been shown to be involved in hippocampal long-term depression (Mulkey, et al. 1994, Nature 369, 486–488).

The role of CAML in these various regulatory processes may be determined using the probes provided for in this invention. Employing the protein and nucleic acid compositions, one may monitor the expression of CAML, enhance or diminish the expression of CAML or change the regulation of CAML expression. In this way one can determine what pathways are controlled by CAML and the position in the pathway at which CAML exerts its regulatory role. In addition, CAML and its binding to cyclophilin B can be exploited to identify novel drugs, including analogs of known drugs, such as derivatives of cyclosporin A, by screening the drugs for binding to CAML and/or interfering with the complex formation of CAML and cyclophilin B. Targets for treatment mediated by CAML activity can include therapeutic contraception, infertility, learning and memory disorders, and the like.

The following examples are offered by way of illustration and not by way of limitation.

EXPERIMENTAL

EXAMPLE 1. (FIG. 1)

(A) CAML transfection replaces the TCR-stimulation requirement for NF-AT activation.

TAg-jurkat cells co-transfected with the NFAT-SEAP reporter SXNFAT (Bram et al., *Molecular and Cellular Biology* 13, 4760–4769 (1993) and a control plasmid pBJ5 (squares), pBJ-CAML (circles), pBJ-β-tubulin (triangles) were stimulated with 25 ng/ml phorbol ester (PMA) and the indicated amounts of OKT3 (anti-CD3 antibody) bound to plastic. NF-AT-specific transcription is expressed as a percentage of maximal induction by ten μg/ml OKT3 anti-TCR antibody.

(B) CAML induction of NF-AT activity requires PMA.

Jurkat cells were co-transfected with NFAT-SEAP and pBJ-CAML (circles) for the control vector pBJ5 (squares), and stimulated with the indicated amounts of PMA. NF-AT specific transcription is indicated in arbitrary phosphatase assay units.

(C) The block in T-cell activation induced by a dominant-negative p59fyn is bypassed by CAML overexpression.

TAg-jurkat cells were transiently transfected with NFAT-SEAP with or without pBJ-CAML and/or p59fyn(−), a plasmid encoding a kinase negative mutant form of p59fyn. Cells were then treated as indicated, and NFAT-SEAP measured. To control for transfection efficiency, a constitutive promotor was included driving the expression of luciferase (EF-UC) in the assay. Phosphatase normalized to luciferase expression is indicated.

(D) CAML overexpression plus PMA activates NF-AT in spite of lack of Lck.

JCaM1 (Lck-negative Jurkat cells) were transiently transfected with NF-AT-luciferase reporter plasmid and pBJ5 (left) or pBJ-CAML (middle) TA-jurkat cells were transfected with NF-AT-luciferase and pBJ5. After 24 hours cells were stimulated with PMA or OKT3 TCR antibody for six hours and NF-AT-specific luciferase was determined. RSV-SEAP reporter was co-transfected to normalize for transfection efficiency.

EXAMPLE 2. Preparation of Plasmids.

Plasmid pAS-B fused the complete coding sequence of cyclophilin B (Hasel and Sutcliffe, *Nucleic Acid Res.* 18, 4019 (1990); Price et al., *Proc. Natl. Acad. Sci. USA* 88, 1903–7 (1991)) to the DNA binding domain of GAL4 in plasmid pAS1 (Durfee, 1993, supra). A B-lymphocyte cDNA library and the GAL4-activation domain plasmid pACT were screened by the yeast 2-hybrid method using pAS-B as bait (Durfee, 1993, supra). 300,000 transformants gave rise to ten potential positive clones. Positive interacting plasmids were recovered and retransformed into yeast Y153 with various bait fusion plasmids to verify specificity of interaction with cyclophilin B. DNA inserts were excised from the interacting plasmids with restriction endonuclease XhO I and were cloned into expression vector pLX2 for transfection into Jurkat cells.

pLX2 is a derivative of expression vector pBJ5, (Takebe, et al., *Molecular and Cellular Biology* 8, 466–472 (1988)) that contains a strong translation initiation codon which adds the residues M-A-R-G to Xho I inserts. Plasmid pBJ-CAIVIL was made by inserting the entire CAML insert into PLX2. (Similar results were obtained with constructs using the normal CAML initiation codon.) TAg-jurkat cells (Northrop et al., *J. Biol. Chem.* 268, 2917–2923 (1993)) were transiently transfected (Mattila et al., *EMBO J* 9, 4425–4433 (1990)) with the indicated: reporter plasmid and pBJ-CAML or the control plasmid with no insert (pBJ5). After 24 h incubation, cells were stimulated with the indicated amounts of OKT3 (bound to plastic dishes) or 0.5 μM ionomycin and 25 ng/ml phorbol ester for a further 20 h. Supernatants were assayed for secreted phosphatase as in Bram et al., *Molecular and Cellular Biology* 13, 4760–4769 (1993).

After identification of the CAML insert as a clone of interest, its interaction with cyclophilin B was verified by two methods. The independent reporter GAL-lacZ in yeast Y153 were shown to be induced by pAS-B plus pACT-CAML in combination, but not by either separately, thus verifying the formation of the 2-hybrid interaction. Secondly, a reverse swap experiment was performed in which CAML coding sequences were excised and subcloned into pAS1 to encode a GAL4-DNA binding domain-CAML fusion and the cyclophilin B cDNA were subcloned into pACT to encode a GAL4-activation domain-cyclophilin B fusion. Stable transformants of Y153 with these two plasmids allowed growth on histidine-deficient medium due to high-level transcriptional induction of GAL-HIS3, while no growth was caused by either plasmid alone.

EXAMPLE 3. Elucidation of the CAML site of action in T-cell signal transduction; CAML overexpression specifically activates calcium signal-dependent transcription factors by elevating intracellular calcium. (FIG. 2)

(A) CAML action is blocked by CsA or FK506.

Figure 2A:
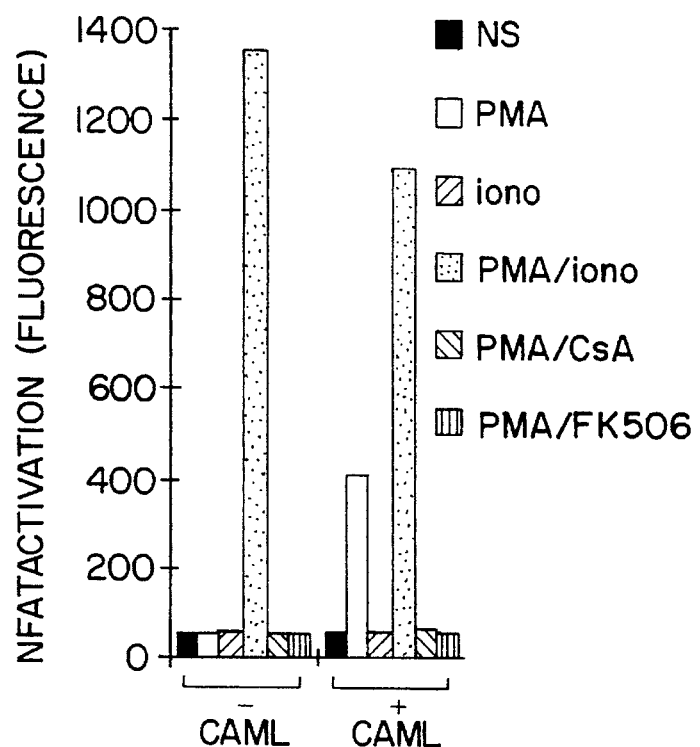
FIGS. 2a–d are concerned with the elucidation of the CAML site of activation in T cell signal transduction; 2(a) is a bar graph showing the effect of CsA or FK506 on CAML action; 2(b) is a bar graph showing CAML action specificity for calcium-dependent transcription factors; 2(c) are FACS plots of cells transfected with a plasmid that directs expression of a cell-surface murine marker (CD8α) and pBJ5 (right) or pBJ-CAML (left); and 2(d) is a graph demonstrating that CAML activation requires cytoplasmic calcium influx.
Figure 2B:
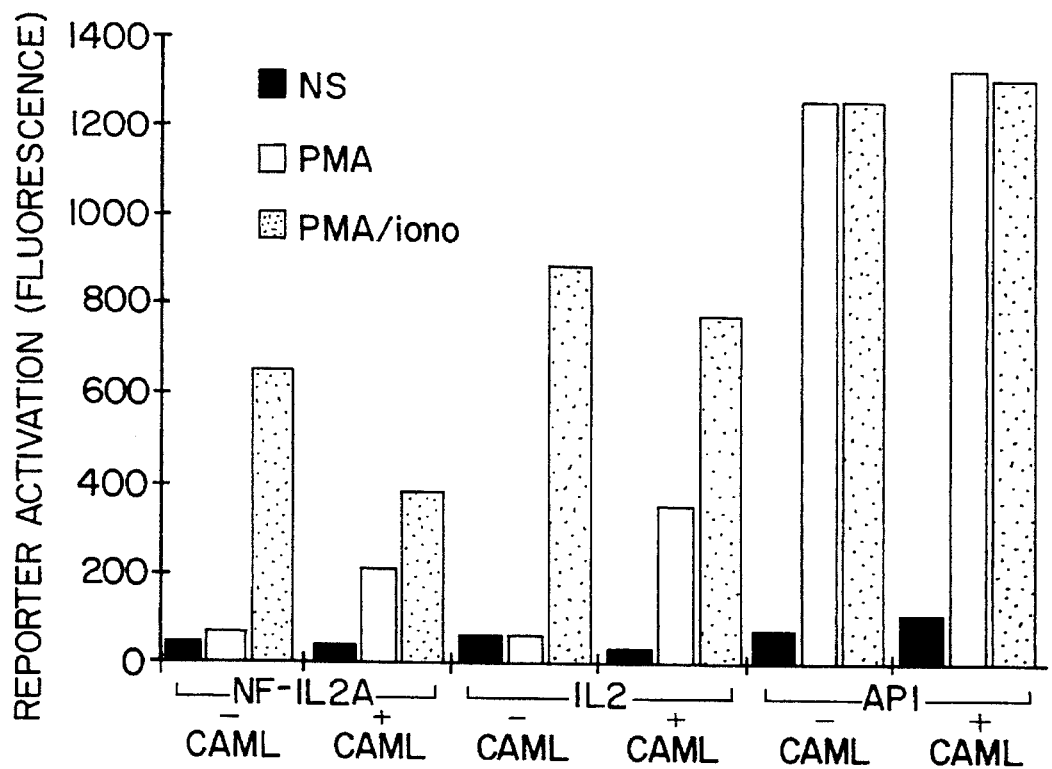
Figures 1, 2C:
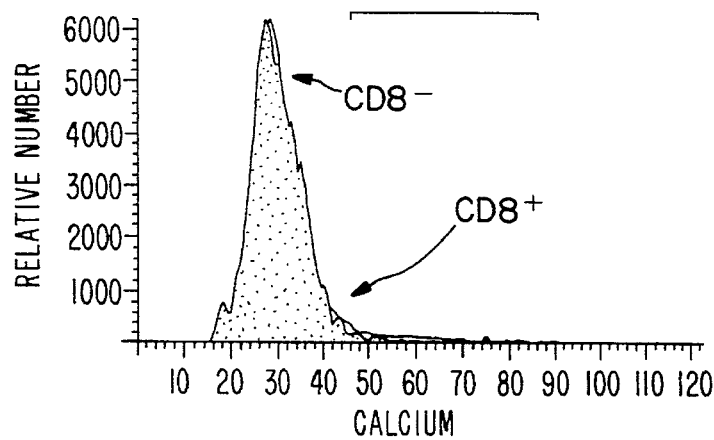
Figures 2, 2C:
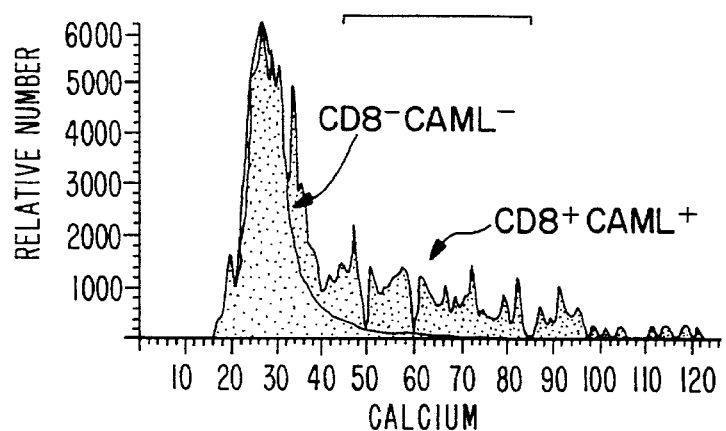
Figure 2D:
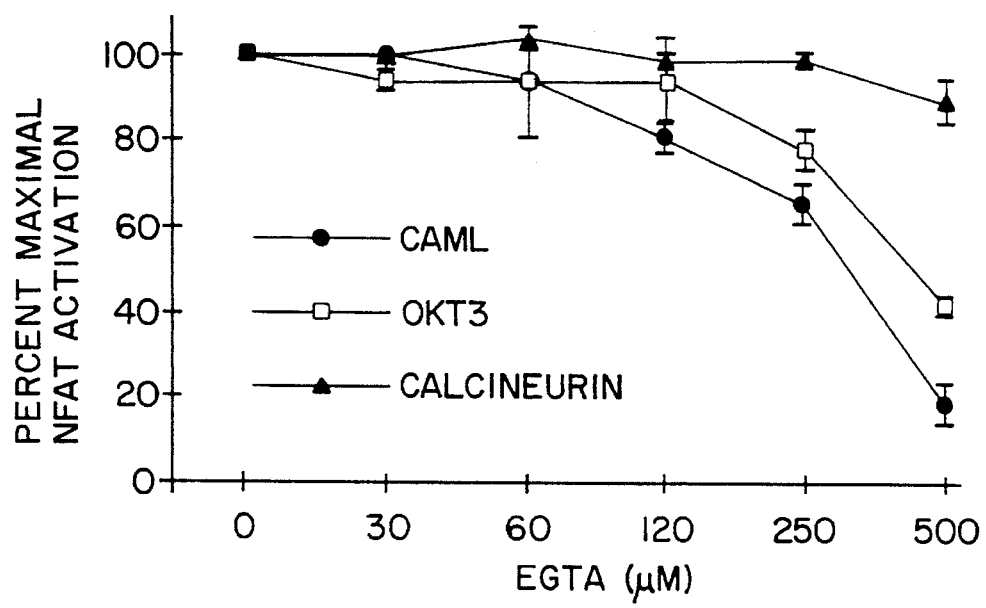

TAg-jurkat cells were co-transfected with NFAT-SEAP reporter plasmid and pBJ5 (left) or pBJ-CAML (right) (see FIG. 2). After 24 h, cells were treated with the indicated combinations of PMA (25 ng/ml), ionomycin (0.5 μM), CsA (100 ng/ml), or FK506 (500 pg/ml) for 20 h and NF-AT specific transcription measured by phosphatase assay.

(B) CAML action is specific for calcium-dependent transcription factors.

TAg-jurkat cells were co-transfected with SEAP reporter plasmids containing control enhancer sequences specific for NF-IL2A, AP-1, or the entire IL-2 enhancer, and with pBJ-CAML or the control plasmid pBJ5. After 24 h, cells were, treated with the indicated combinations of PMA (25 ng/ml) and ionomycin (0.5 μM) for 20 h and NF-AT specific transcription measured by phosphatase assay. Specific induction due to CAML was seen in PMA treated cells transfected with NF-IL2A or IL2 reporter plasmids (open boxes).

(C) Jurkat cells were transiently co-transfected with a plasmid that directs expression of a cell-surface marker (murine CD8α) and plasmid pBJ5 (left) or pBJ-CAML (right).

Control experiments were done to ensure that CD8α overexpression did not inhibit or stimulate T-cell activation by CAML. After 24 h incubation at 37° C., cells were loaded with INDO-1 and stained with FITC-labeled antibody to murine CD8α (Becton-Dickenson, *Anti-LYT2*) to identify the transfected cells. Individual cell calcium and FITC fluorescence were measured with a Becton-Dickenson Facs Star P+. Cells were warmed to 37° C. and treated with 25 ng/ml PMA immediately prior to analysis. For each plot, the CD8α brightest 1% of cells representing the transfected cells are shown by the shaded curve, while untransfected cells in the same culture are shown by the unshaded line. The bracket overlying each plot indicates the intracellular calcium level in cells treated with 1 µM ionomycin at the end of the experiment.

(D) CAML activation of NF-AT requires extracellular calcium.

TAg-jurkat cells were co-transfected with NFAT-SEAP and pBJ5 (square), pBJ-CAML (circles) or pBJ-MutCin (triangles), a plasmid directing expression of C-terminal truncated, calcium-independent calcineurin A subunit (Clipstone and Crabtree, Ann. of N.Y. Acad. Sci. 696, 20–31 (1993)). Cells were grown for 24 h and subsequently stimulated by addition of 25 ng/ml PMA (circles and triangles) or 25 ng/ml PMA+ 10 µg/ml OKT3 antibody to the TCR (squares), in the presence of the indicated levels of EGTA. Averages and standard deviations from two separate experiments are shown.

RESULTS

The screening of a human lymphocyte cDNA library (Durfee, 1993, supra) for clones encoding cyclophilin-binding proteins using the yeast 2-hybrid system with cyclophilins A or B fused to the DNA-binding domain of GAL4 as the interaction target, resulted in cyclophilin A being relatively non-selective in the assay (1:1,000 clones), whereas cyclophilin B was highly selective (1:30,000 clones). Plasmids from ten yeast colonies that were positive for interaction following re-screening with cyclophilin B were further analyzed.

Overexpression of the cyclophilin B interacting protein encoded by one cDNA clone (CAML) partially abolished the requirements for TCR cross-linking as judged by activation of NF-AT specific transcription, when assayed in the presence of PMA to provide a co-stimulatory signal. The degree of NF-AT activation by CAML varied from 20–125% of maximal (PMA plus ionomycin)induction in multiple transfections, whereas in control transfections, activation of NF-AT was not observed in cells stimulated by PMA alone.

Activation of NF-AT by CAML requires exogenous stimulation of phosphokinase C by PMA, indicating that CAML acts downstream of the TCR and phospholipase C. The data also demonstrate that CAML acts downstream from the tyrosine kinases Fyn and Lck. Based on the evidence obtained with CsA and FK506, where immunosuppressive amounts of either drug completely abolished CAML-mediated activation, CAML acts upstream from calcineurin.

Transfection with the CAML overexpression plasmid, with various enhancer sequences demonstrated that CAML partly replaces the calcium influx requirement for both NF-IL2A and the entire IL2 enhancer, in a fashion similar to its effect with NF-AT. The degree of stimulation varies from 20–60% of the maximal stimulation (see above). CAML overexpression does not affect the activity of the calcium-independent transcription factor AP1.

CAML activation may be dependent upon external calcium, in light of the results obtained with EGTA in the medium, or may be dependent on internal calcium stores.

Assay for CAML expression

Preparation of plate and reagents

Nunc Maxisorb plates are coated with an anti-CAML IgM antisera. The coating solution is 10 µg/ml of antisera in 0.1M Na Acetate. Each well is coated with 100 µl of coating solution and incubated for 6± 0.5 hours at 25° C., ±98% relative humidity. At the end of the incubation the coating solution is aspirated and the wells rinsed once with 50 mM phosphate buffer at 300 µl/well. Then the wells are blocked with 1% bovine serum albumin at 300 µl/well for 18±4 hours at 25° C., ±98% relative humidity. At the end of incubation the blocking solution is aspirated and the plates washed once with 50 mM phosphate buffer at 300 µl/well. Then the plates are coated with 4% sucrose solution at 300 µl/well for 10 minutes. The sucrose solution is aspirated from all the wells. The plates are dried in a drying tunnel for 7 minutes at 52° C.

Conjugate

Horse radish peroxidase (HRP) conjugate of goat anti-mouse IgG is diluted 1:8,000 in assay buffer.

Substrate

OPD (o-phenylenediamine) solution is prepared fresh prior to use within 15 minutes at 3 mg/ml in the assay buffer.

Assay Protocol:

Diluted supernatant of a cellular lysate, which has been centrifuged to remove debris, is pipetted into each test well, 100 µl/well. 50 mM phosphate buffer, 0.01.% thimerosal pH7.4 is added into each well, 100 µl/well. The plate is covered with plastic sealer and incubated at 37° C. for one hour.

The plate is aspirated and washed 3 times with buffer, 325 µl/well each time.

Mouse anti-CAML antisera is added to each well at a dilution of 1:4000, 100 µl/well, and the mixture incubated for 30 min followed by aspiration and washing, as described above.

Diluted goat anti-mouse IgG-HRP conjugate is pipetted into all wells. The plate is incubated at room temperature for one hour.

The plate is aspirated and washed 3 times with buffer, 325 µl/well each time.

OPD substrate solution is pipetted into all wells. The plate is incubated for 7 minutes at room temperature.

Stop solution is added into all wells, 100 µl/well.

The plate is read in a microplate reader at a wavelength of 492 nm and 600 nm reference wavelength.

Following the above procedure, human T cells activated by binding of antibodies to the T cell receptor are assayed for the expression of CAML. Activated T cells give a stronger CAML signal than quiescent T cells indicating that activation enhances CAML expression.

It is evident from the results, that the subject invention provides novel compositions which can be used in the elucidation in the calcium-dependent activation pathway for expression of a number of different genes. Particularly, the subject compositions can be used in the investigation of T-cell activation. Agents may be screened for their effect on the role of CAML in cellular processes, where the agents may serve as therapeutic agents in modulating the activation of a variety of cells and controlling the expression of calcium-dependent transcription.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated DNA of at least 18 bp encoding calcium-signal modulating cyclophilin (CAML) having at least 60% similarity to SEQ ID: No 1.

2. An isolated DNA according to claim 1, comprising the sequence of SEQ ID: NO 1 or having at least 75% similarity to said sequence.

3. An isolated cDNA according to claim 2, comprising the sequence of SEQ ID: NO 1.

4. A cell comprising an expression cassette comprising a gene encoding, said expression cassette being integrated at a site other than the natural site for said gene as a result of the introduction of DNA comprising said expression cassette into said cell and progeny cells thereof.

5. A cell according to claim 4, wherein said cell is a mammalian cell and said expression cassette comprises a promoter other than the CAML promoter.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1391 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 37..927

( x i ) SEQUENCE DESCRIPTION: SEQ ID NO:1:

```
CGCCACTGCC ACCCCTCCCA GACTGTGGAC GGGAGG ATG GAG TCG ATG GCC GTC       54
                                       Met Glu Ser Met Ala Val
                                         1               5

GCT ACC GAC GGC GGG GAG AGG CCG GGG GTC CCA GCG GGC TCA GGT CTG      102
Ala Thr Asp Gly Gly Glu Arg Pro Gly Val Pro Ala Gly Ser Gly Leu
             10                  15                  20

TCG GCT TCC CAG CGT CGG GCG GAG CTG CGT CGG AGA AAG CTG CTC ATG      150
Ser Ala Ser Gln Arg Arg Ala Glu Leu Arg Arg Arg Lys Leu Leu Met
         25                  30                  35

AAC TCG GAA CAG CGC ATC AAC CGG ATC ATG GGC TTT CAC AGG CCC GGG      198
Asn Ser Glu Gln Arg Ile Asn Arg Ile Met Gly Phe His Arg Pro Gly
     40                  45                  50

AGC GGC GCG GAA GAA GAA AGT CAA ACA AAA TCA AAG CAG CAG GAC AGT      246
Ser Gly Ala Glu Glu Glu Ser Gln Thr Lys Ser Lys Gln Gln Asp Ser
 55                  60                  65                  70

GAT AAA CTG AAC TCC CTC AGC GTT CCT TCC GTT TCA AAG CGA GTA GTG      294
Asp Lys Leu Asn Ser Leu Ser Val Pro Ser Val Ser Lys Arg Val Val
                 75                  80                  85

CTG GGT GAT TCA GTC AGT ACA GGA ACA ACT GAC CAG CAG GGT GGT GTG      342
Leu Gly Asp Ser Val Ser Thr Gly Thr Thr Asp Gln Gln Gly Gly Val
             90                  95                 100

GCC GAG GTA AAG GGG ACC CAA CTG GGA GAC AAA TTG GAC TCG TTC ATT      390
Ala Glu Val Lys Gly Thr Gln Leu Gly Asp Lys Leu Asp Ser Phe Ile
         105                 110                 115

AAA CCA CCT GAG TGC AGT AGT GAT GTC AAC CTT GAG CTC CGG CAG CGG      438
Lys Pro Pro Glu Cys Ser Ser Asp Val Asn Leu Glu Leu Arg Gln Arg
     120                 125                 130

AAC AGA GGG GAC CTG ACA GCG GAC TCG GTC CAG AGG GGT TCC CGC CAT      486
Asn Arg Gly Asp Leu Thr Ala Asp Ser Val Gln Arg Gly Ser Arg His
135                 140                 145                 150

GGC CTA GAG CAG TAC CTT TCC AGA TTC GAA GAA GCA ATG AAG CTA AGG      534
Gly Leu Glu Gln Tyr Leu Ser Arg Phe Glu Glu Ala Met Lys Leu Arg
                 155                 160                 165

AAA CAG CTG ATT AGT GAA AAA CCC AGT CAA GAG GAT GGA AAT ACA ACA      582
Lys Gln Leu Ile Ser Glu Lys Pro Ser Gln Glu Asp Gly Asn Thr Thr
             170                 175                 180

GAA GAA TTT GAC TCT TTT CGA ATA TTT AGA TTG GTG GGA TGT GCT CTT      630
Glu Glu Phe Asp Ser Phe Arg Ile Phe Arg Leu Val Gly Cys Ala Leu
             185                 190                 195

CTT GCT CTT GGA GTC AGA GCT TTT GTT TGC AAA TAC TTG TCC ATA TTT      678
Leu Ala Leu Gly Val Arg Ala Phe Val Cys Lys Tyr Leu Ser Ile Phe
 200                 205                 210
```

```
GCT CCA TTT CTT ACT TTA CAA CTT GCG TAC ATG GGA TTA TAC AAA TAT        726
Ala Pro Phe Leu Thr Leu Gln Leu Ala Tyr Met Gly Leu Tyr Lys Tyr
215                 220                 225                 230

TTT CCC AAG AGT GAA AAG AAG ATA AAG ACA ACA GTA CTA ACA GCT GCA        774
Phe Pro Lys Ser Glu Lys Lys Ile Lys Thr Thr Val Leu Thr Ala Ala
                235                 240                 245

CTT CTA TTG TCG GGA ATT CCT GCC GAA GTG ATA AAT CGA TCA ATG GAT        822
Leu Leu Leu Ser Gly Ile Pro Ala Glu Val Ile Asn Arg Ser Met Asp
            250                 255                 260

ACC TAT AGC AAA ATG GGC GAA GTC TTC ACA GAT CTC TGT GTC TAC TTT        870
Thr Tyr Ser Lys Met Gly Glu Val Phe Thr Asp Leu Cys Val Tyr Phe
        265                 270                 275

TTC ACT TTT ATC TTT TGT CAT GAA CTG CTT GAT TAT TGG GGC TCT GAA        918
Phe Thr Phe Ile Phe Cys His Glu Leu Leu Asp Tyr Trp Gly Ser Glu
    280                 285                 290

GTA CCA TGAAGCCTGT AGAACTGAGA AGGAGAAGCT TACGAAAAAA ATCCTCTTCT         974
Val Pro
295

ATATTGCAGT GTCTCTAAAG GAGGCAAATT GGTTTACACC TTCATGTAAT TCTTTTACTT     1034

TAGGGGTTGT AAAGCTACTT TATTAGATAT AGAATGGCAG ATTCTCTGAT TTAAAAGGGC     1094

TGAGTTTGTA TTATTACTGA TATGAAGAAT AGAGTACCAA TGTCATTAAT TGATTTTCT      1154

TGTTAATCAG AATTCCTATT CTGTACCTTT CCTCTAACTT CTCAGATTTG TAATTCTTCT     1214

TTTCGGGAGC TGAGCTAGTG CTTTTAGGAG AACAGATAAA TGTGGTCTCA GCCAGCCCTA     1274

GAGACTGCTT CTTGTGTTTG TGTCATTCTG TCCTGAGAAA TGAAGTCATC TGAAAAATAA     1334

AAATGCAGAA ACCCAAAAAA AAAAAAAAAA AAAAAAAAAA AAAAAAAAAA AAAAAA         1391
```

( 2 ) INFORMATION FOR SEQ ID NO:2:

( i ) SEQUENCE CHARACTERISTICS:
        ( A ) LENGTH: 296 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Ser Met Ala Val Ala Thr Asp Gly Gly Glu Arg Pro Gly Val
 1               5                  10                  15

Pro Ala Gly Ser Gly Leu Ser Ala Ser Gln Arg Arg Ala Glu Leu Arg
                20                  25                  30

Arg Arg Lys Leu Leu Met Asn Ser Glu Gln Arg Ile Asn Arg Ile Met
            35                  40                  45

Gly Phe His Arg Pro Gly Ser Gly Ala Glu Glu Ser Gln Thr Lys
        50                  55                  60

Ser Lys Gln Gln Asp Ser Asp Lys Leu Asn Ser Leu Ser Val Pro Ser
65                  70                  75                  80

Val Ser Lys Arg Val Val Leu Gly Asp Ser Val Ser Thr Gly Thr Thr
                85                  90                  95

Asp Gln Gln Gly Gly Val Ala Glu Val Lys Gly Thr Gln Leu Gly Asp
               100                 105                 110

Lys Leu Asp Ser Phe Ile Lys Pro Pro Glu Cys Ser Ser Asp Val Asn
           115                 120                 125

Leu Glu Leu Arg Gln Arg Asn Arg Gly Asp Leu Thr Ala Asp Ser Val
       130                 135                 140

Gln Arg Gly Ser Arg His Gly Leu Glu Gln Tyr Leu Ser Arg Phe Glu
145                 150                 155                 160
```

```
Glu Ala Met Lys Leu Arg Lys Gln Leu Ile Ser Glu Lys Pro Ser Gln
                165             170             175
Glu Asp Gly Asn Thr Thr Glu Glu Phe Asp Ser Phe Arg Ile Phe Arg
            180             185             190
Leu Val Gly Cys Ala Leu Leu Ala Leu Gly Val Arg Ala Phe Val Cys
        195             200             205
Lys Tyr Leu Ser Ile Phe Ala Pro Phe Leu Thr Leu Gln Leu Ala Tyr
    210             215             220
Met Gly Leu Tyr Lys Tyr Phe Pro Lys Ser Glu Lys Lys Ile Lys Thr
225             230             235             240
Thr Val Leu Thr Ala Ala Leu Leu Leu Ser Gly Ile Pro Ala Glu Val
            245             250             255
Ile Asn Arg Ser Met Asp Thr Tyr Ser Lys Met Gly Glu Val Phe Thr
            260             265             270
Asp Leu Cys Val Tyr Phe Phe Thr Phe Ile Phe Cys His Glu Leu Leu
        275             280             285
Asp Tyr Trp Gly Ser Glu Val Pro
    290             295
```